United States Patent
Lowe et al.

(10) Patent No.: US 9,726,618 B2
(45) Date of Patent: Aug. 8, 2017

(54) SENSING SYSTEM AND METHOD

(75) Inventors: Christopher Robin Lowe, Cambridge (GB); Karishma Jain, Cambridge (GB); Adrian Carl Stevenson, Cambridge (GB)

(73) Assignee: PARAMATA LTD., Cambridge, Cambridgeshire (GB)

( * ) Notice: Subject to any disclaimer, the term of this patent is extended or adjusted under 35 U.S.C. 154(b) by 439 days.

(21) Appl. No.: 13/697,597

(22) PCT Filed: May 16, 2011

(86) PCT No.: PCT/GB2011/050936
§ 371 (c)(1),
(2), (4) Date: Jan. 28, 2013

(87) PCT Pub. No.: WO2011/141755
PCT Pub. Date: Nov. 17, 2011

(65) Prior Publication Data
US 2013/0139596 A1   Jun. 6, 2013

(30) Foreign Application Priority Data

May 14, 2010   (GB) .................................. 1008139.6

(51) Int. Cl.
*G01N 22/02*    (2006.01)
*G01R 27/32*    (2006.01)
*G01N 33/44*    (2006.01)

(52) U.S. Cl.
CPC ........... *G01N 22/02* (2013.01); *G01N 33/442* (2013.01)

(58) Field of Classification Search
CPC ...... G01N 22/02; G01N 33/442; G01R 27/04; G01R 27/32

(Continued)

(56) References Cited

U.S. PATENT DOCUMENTS 3,973,146 A * 8/1976 Arnold et al. ................. 257/254
4,045,727 A * 8/1977 Yu ............................. G01V 3/08
324/644

(Continued)

FOREIGN PATENT DOCUMENTS

| EP | 2065681 | 6/2009 | |
| JP | 2010-107259 | 5/2010 | |
| WO | WO 2009068886 A2 * | 6/2009 | ............... G01D 1/00 |

OTHER PUBLICATIONS

Kharkovsky et al., "Application of near-field microwave and millimeter wave nondestructive testing for evaluation of fiber breakage and orientation evaluation in CFRP", . . . .

*Primary Examiner* — Michael A Lyons
*Assistant Examiner* — Suman K Nath
(74) *Attorney, Agent, or Firm* — Welsh Flaxman & Gitler LLC

(57) ABSTRACT

A sensing system which comprises a material (30) formed of a matrix and a plurality of non-insulating particles (40) substantially equally spaced within the matrix such that the material has coherent electrical periodicity in at least one dimension; and a receiver (10), the receiver arranged to receive a source RF signal and a returned RF signal, the source RF signal being reflected by the non-insulating particles to produce the returned RF signal. A change in the position of one or more of the non-insulating particles causes the returned RF signal to change, such that a change in a property of the material can be determined from the returned RF signal.

28 Claims, 16 Drawing Sheets

(58) Field of Classification Search
USPC .......... 73/582, 579, 601, 643; 324/637, 639
See application file for complete search history.

(56) References Cited

U.S. PATENT DOCUMENTS

| | | | | |
|---|---|---|---|---|
| 5,808,473 | A * | 9/1998 | Shinagawa et al. | 324/754.02 |
| 5,859,364 | A * | 1/1999 | Toda | B82Y 20/00 73/105 |
| 7,439,749 | B2 * | 10/2008 | Zoughi | G01N 22/02 324/637 |
| 7,947,773 | B2 * | 5/2011 | Hansen | B29C 70/14 264/104 |
| 8,736,281 | B2 * | 5/2014 | Lowe | G01D 5/12 324/326 |
| 2002/0154029 | A1 * | 10/2002 | Watters et al. | 340/870.07 |
| 2005/0200373 | A1 * | 9/2005 | Yakymyshyn et al. | 324/754 |
| 2006/0005615 | A1 * | 1/2006 | Ducker | B82Y 35/00 73/105 |
| 2007/0046298 | A1 * | 3/2007 | Safai | G01N 22/02 324/639 |
| 2008/0315871 | A1 * | 12/2008 | Lepage et al. | 324/242 |
| 2009/0079644 | A1 * | 3/2009 | May | H01Q 19/06 343/753 |
| 2009/0302866 | A1 * | 12/2009 | Xiang | B82Y 20/00 324/636 |
| 2012/0007607 | A1 * | 1/2012 | Lowe et al. | 324/639 |

\* cited by examiner (A)

(B)

(C)

SENSING SYSTEM AND METHOD

The present invention relates to a sensing system and method.

Structural health monitoring (SHM) is a field of technology that is attracting increasing interest in industries such as civil, structural and aerospace engineering. The aim of SHM is to collect data concerning critical structural elements using sensors, in order to provide indicators of anomalies detected in a structure, thereby monitoring its reliability and safety.

SHM is particularly relevant to areas of technology where composite materials are increasingly used. Existing composite materials include fibre reinforced polymer composites which have a high strength-to-weight ratio, good stiffness properties, inherent corrosion resistance, and low electromagnetic reflectance. These properties have made fibre reinforced composites an attractive material for primary aircraft structures, increasingly replacing metal components.

Other industries in which composite materials are increasingly used are the oil and gas industry, in which monitoring of the fatigue of components such as seals and gaskets is critical, underground structures such as tunnels and pipeline networks, and military aircraft and submarine technology, where reliability and safety are paramount.

SHM is also relevant to the medical sector where implanted components, heart valves and hip joints need to be monitored for reliability and safety; for environmental sensing where contamination in water or air can be tracked with robust materials at low cost; for Advanced Manufacturing where materials, especially composite materials, can be tracked during the production process, to raise the quality of plastic parts; and for applications in hostile or inaccessible locations such as space or those using rotary components such as wind turbines/blades.

The areas of technology described above could benefit from reliable and accurate wireless sensing in order to selectively or continuously monitor structures that are not immediately accessible for close inspection.

A number of SHM methods are known. Radiography, which uses X-rays to form an image which is related to the density of the material, has been available for over a century, however this method is hazardous and therefore rarely used. Thermal imaging or vibrothermography is a proven method of detection of disbands and delaminations by monitoring the transfer of thermal energy in the infrared spectrum. A disadvantage of thermal imaging, however, is the difficulty of interpreting the results. Laser shearography and holography imaging, which may be used to assess the strength of the inspected material, are advantageously non-contact techniques, however they suffer from image noise due to vibration.

Other SHM methods, only applicable to metallic/ferrous metal structures use fluorescent or magnetic particle penetrants. Note that metal inspection can use Eddy current detection methods, however such methods may not be used in composite materials. Due to the heterogenous nature of composites, the form of defects is often very different from those typically found in a metallic material, and the fracture mechanisms are more complex.

Current SHM systems require the installation of one or more sensors at key points of any structure of interest, the type of sensor depending on specific parameters of interest to be sensed. This can make such systems expensive and time consuming to install, while real time, continuous monitoring of the sensors is in practice unrealistic.

The most desirable SHM method for detecting damage in composite materials is acoustics, or tracking the radio properties of multiple particles, thereby forming intrinsic sensors. An intrinsic sensor is a structural material (normally a composite) that has radio properties according to its mechanical status (which, according to the specific material, is related to temperature, pressure, hydration etc). The surface or volume of such materials can be mapped as an image for SHM.

However, a radio signal directed at a regular composite material is unable to extract information about the mechanical, electrical and chemical status of the material. Therefore, existing intrinsic sensors require the addition of sensing elements whose electron distribution and/or transport properties are altered by their local environment in order to make this monitoring function possible.

The sensing elements are arranged to alter properties such as the dielectric or magnetic properties of the material. For example, an embedded piezoelectric particle which has a vibrational frequency perturbed by damage may be tracked using radio waves. By detecting this vibrational frequency at several points in the material, a frequency image may be created in order to inspect the damage.

A disadvantage of such intrinsic sensors however is that they require the addition of separate, discrete sensing elements, not being applicable to regular composite materials increasingly used in a large number of applications described above, in particular in aerospace systems.

The present invention therefore seeks to provide a sensing system and method able to use regular composite materials which do not require any additional sensing elements.

According to the present invention there is provided a sensing system which comprises:

a material comprising a matrix and a plurality of non-insulating particles substantially equally spaced within the matrix such that the material has coherent electrical periodicity in at least one dimension; and a receiver arranged to receive a source RF signal and a returned RF signal, the source RF signal being reflected by the non-insulating particles to produce the returned RF signal;

wherein a change in the position of one or more of the non-insulating particles causes the returned RF signal to change, such that a change in a property of the material can be determined from the returned RF signal.

The matrix may be a non-conductive matrix and the non-insulating particles may be conducting particles. The conductive particles may be carbon particles, carbon fibre, graphenes, aluminium particles, silver particles, copper particles, gold particles, or carbon nanotubes. Alternatively, the non-insulating particles may be semiconducting particles or they may be composite particles comprising a metal and an insulator.

The insulating matrix may comprise a polymer, such as a thermosetting epoxy, thermoplastic polyester, vinyl ester or nylon.

The material may have a coherent periodic conductivity or coherent periodic dielectric constant in at least one dimension.

The change in the returned RF signal may be a change in amplitude, a change in frequency, a phase-shift, or a change in interference effects, which relates to measuring composite charge. The detected change in a property of the material may be any of a particle break, a microcrack, a delamination, a contaminant, matrix impact damage, or porosity.

The receiver is further arranged to receive ambient signals (separate from the source signals) which are also picked up by the composite material.

The present invention also provides a method of sensing a change in a property of a material, the material comprising a matrix and a plurality of non-insulating particles substantially equally spaced within the matrix such that the material has coherent electrical periodicity in at least one dimension, the method comprising the steps of:

interrogating the material with a source RF signal;

receiving a returned RF signal reflected from the non-insulating particles;

and determining the change in the property of the material from a change in the returned RF signal that is caused by a change in the position of one or more of the non-insulating particles.

Interrogating the material may comprise scanning the surface of the material using a single mechanical probe or with an electronic multiple probe. The probe may be a 2D probe array with electronic switching or multiple signal channels.

Interrogating the material may comprise exciting the material as though it was an antenna to generate a surface field profile. The material may comprise a plurality wherein each cell represents an antenna element. The plurality of cells may be coupled to form a cell array, for example via induced modulated RF currents. In preferred embodiments, the probe array comprises at least one high impedance probe and the returned RF signal is received by a homodyne receiver.

Interrogating the material may further comprise scanning the surface field profile using a single mechanical probe. Interrogating the material may further comprise scanning the surface field profile using an electronic multiple probe.

The source RF signal may be pulse modulated or modulation or modulation may be by other digital or analogue methods.

The material may be obtained by doping a semiconductor material to achieve the coherent electrical periodicity.

By using regular composite materials and not requiring the embedding of sensing materials, the present invention has the advantage that it may be used in more familiar applications, including SHM applications. Moreover, the sensing materials of the present invention are often already available. For example, certain carbon fibre laminate structures used for aerospace applications are quasi crystals which form an ordered lattice like structure.

The present invention can select the low frequency part of the electromagnetic spectrum to penetrate into the composite and directly interact with the damage. This provides an advantage relative to the competitive approaches mentioned above, such as shearography or IR which look at the surface for indirect evidence of sub surface damage. Acoustics also has this advantage as it directly interacts with the damage. The acoustic signal penetrates into the composite SHM structure/architecture to reveal sub surface damage by wave scattering off acoustic impedance perturbations that are in turn a consequence of the damage itself. Similarly, the electromagnetic approach according to the present invention excites an electromagnetic wave mode that is perturbed by boundary discontinuities.

The invention will now be described in detail with reference to the accompanying drawings, in which.

Figure 9:
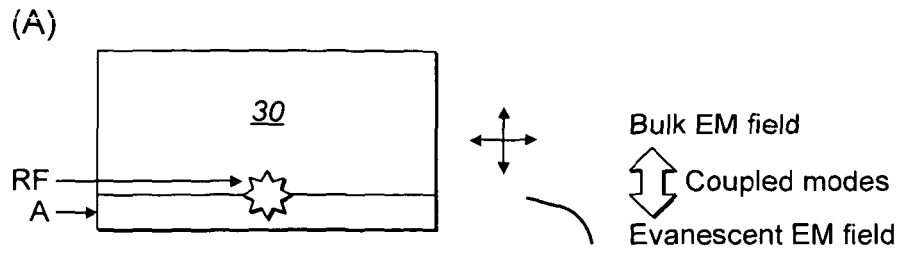
Figure 9:
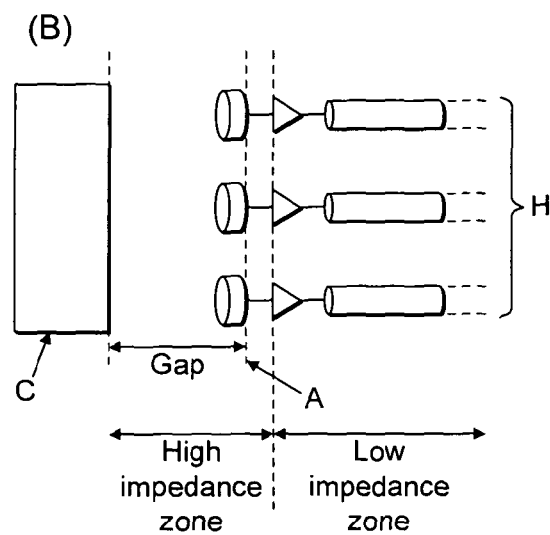
Figure 9:
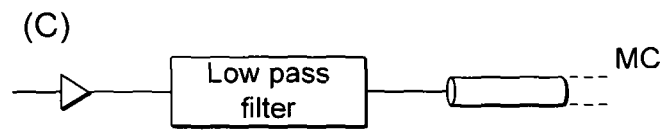
Figure 9:
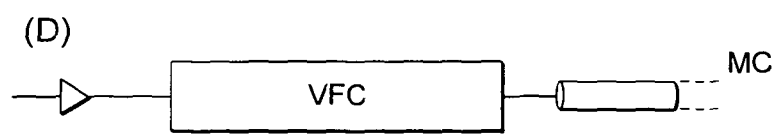
Figure 9:
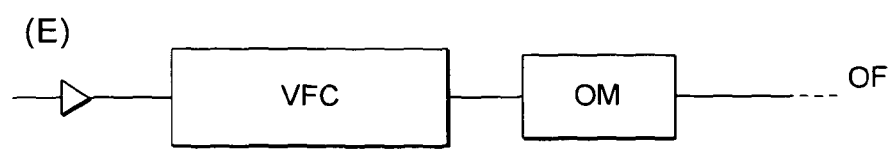
Figure 10:
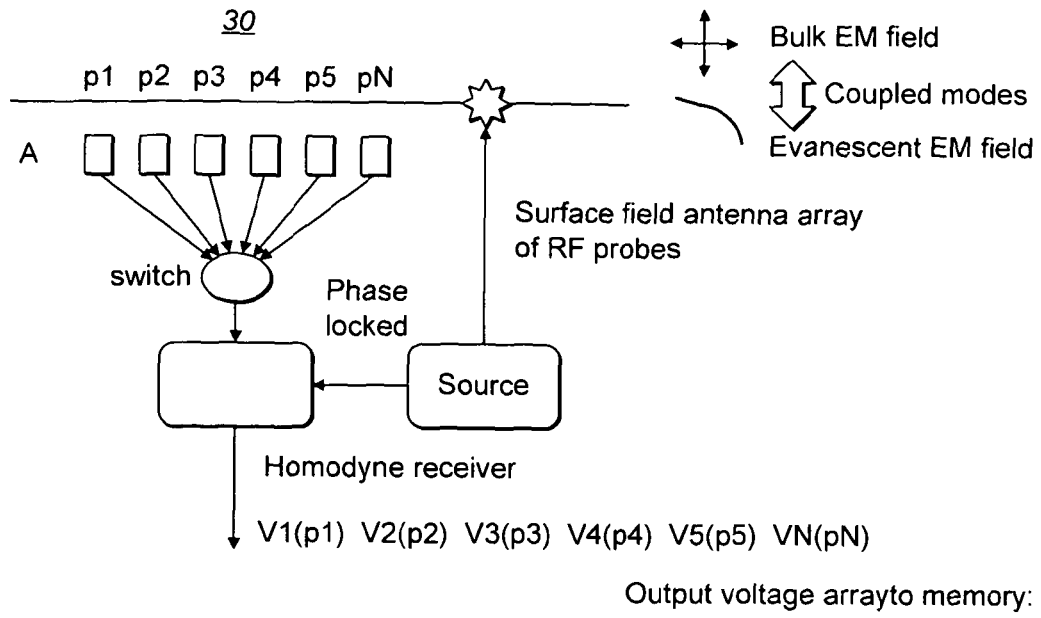
Figure 11:
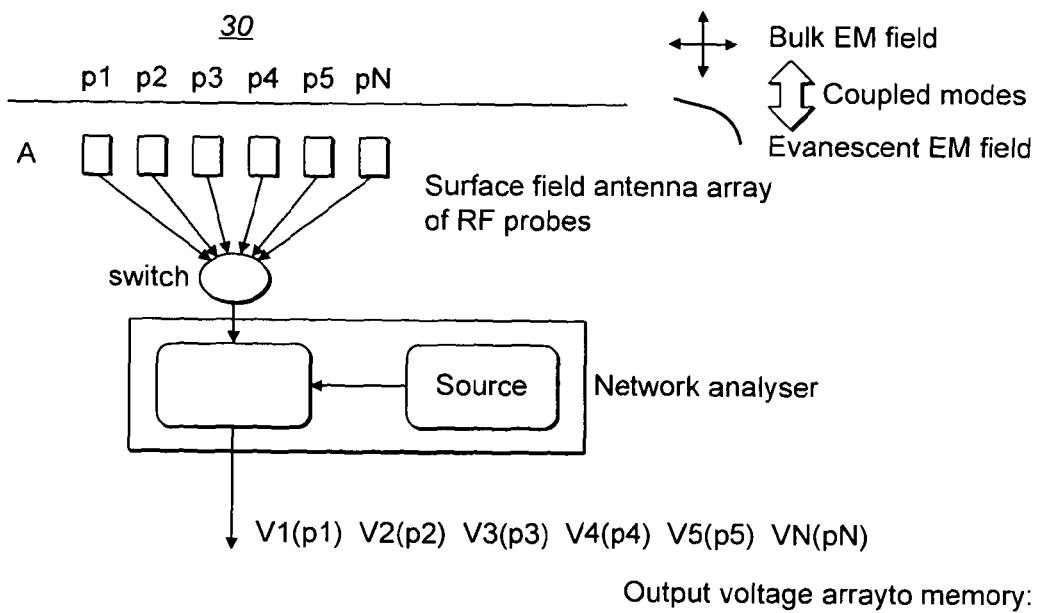
Figure 12:
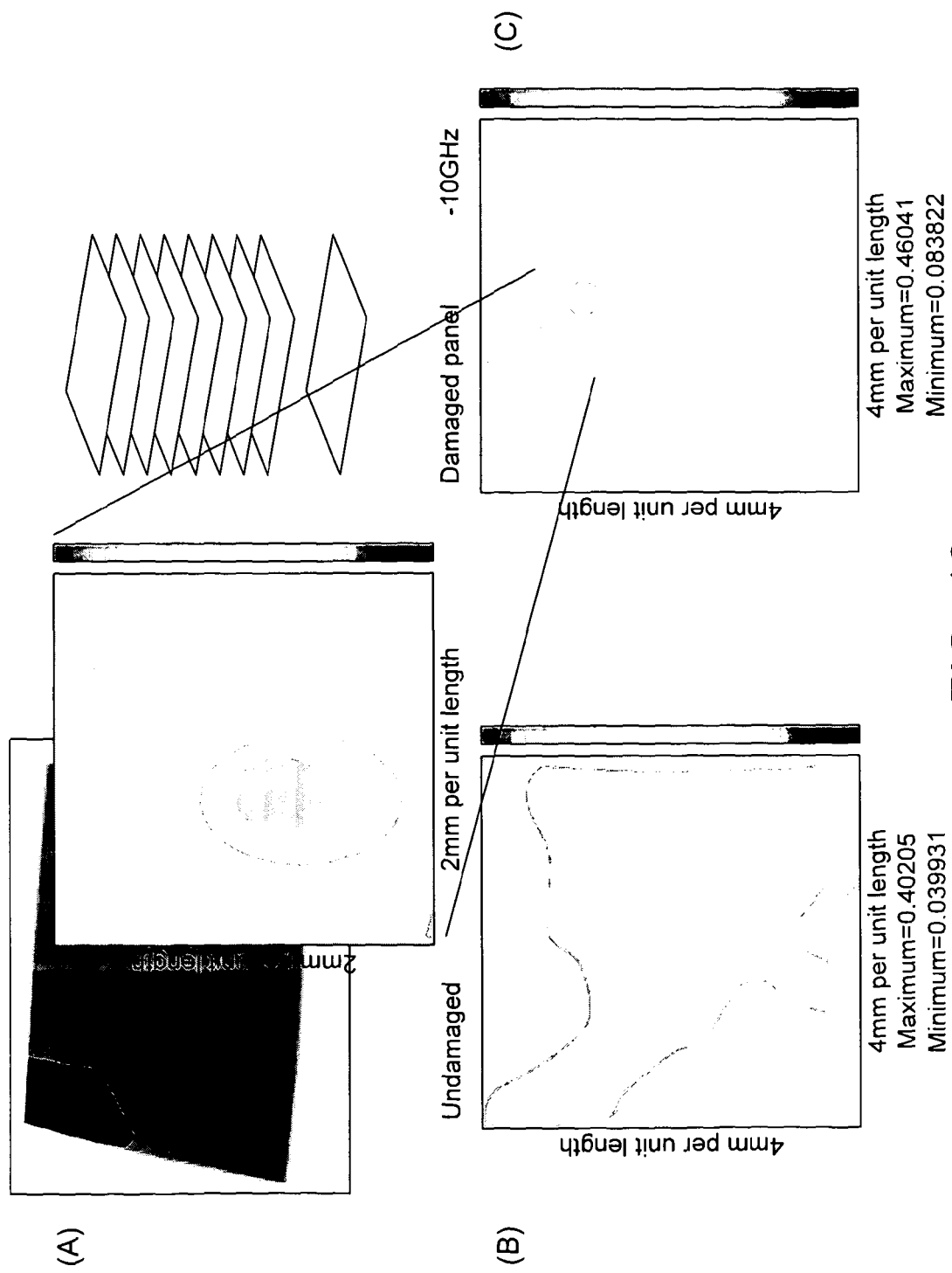
Figure 12:
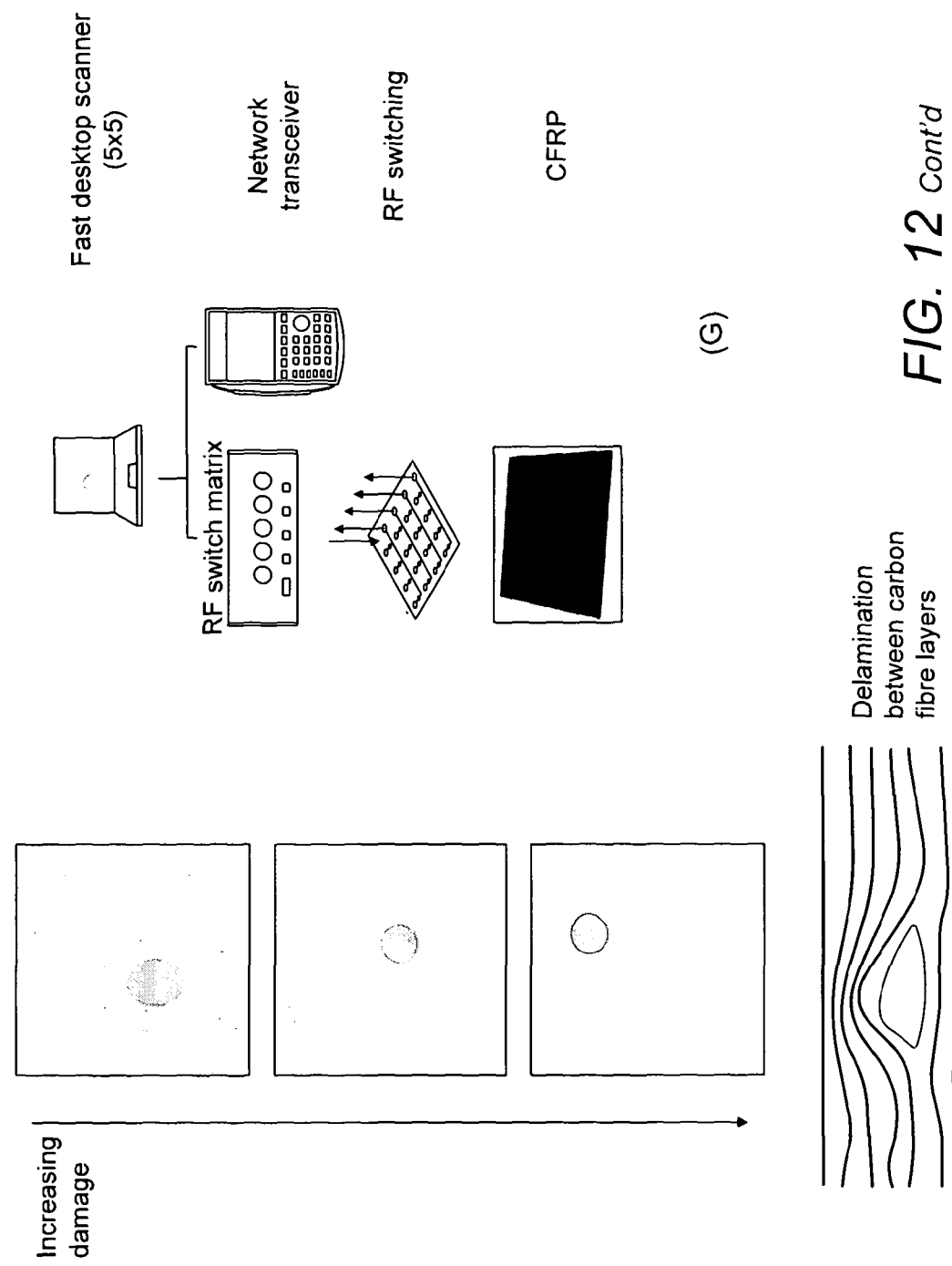
Figure 13A:
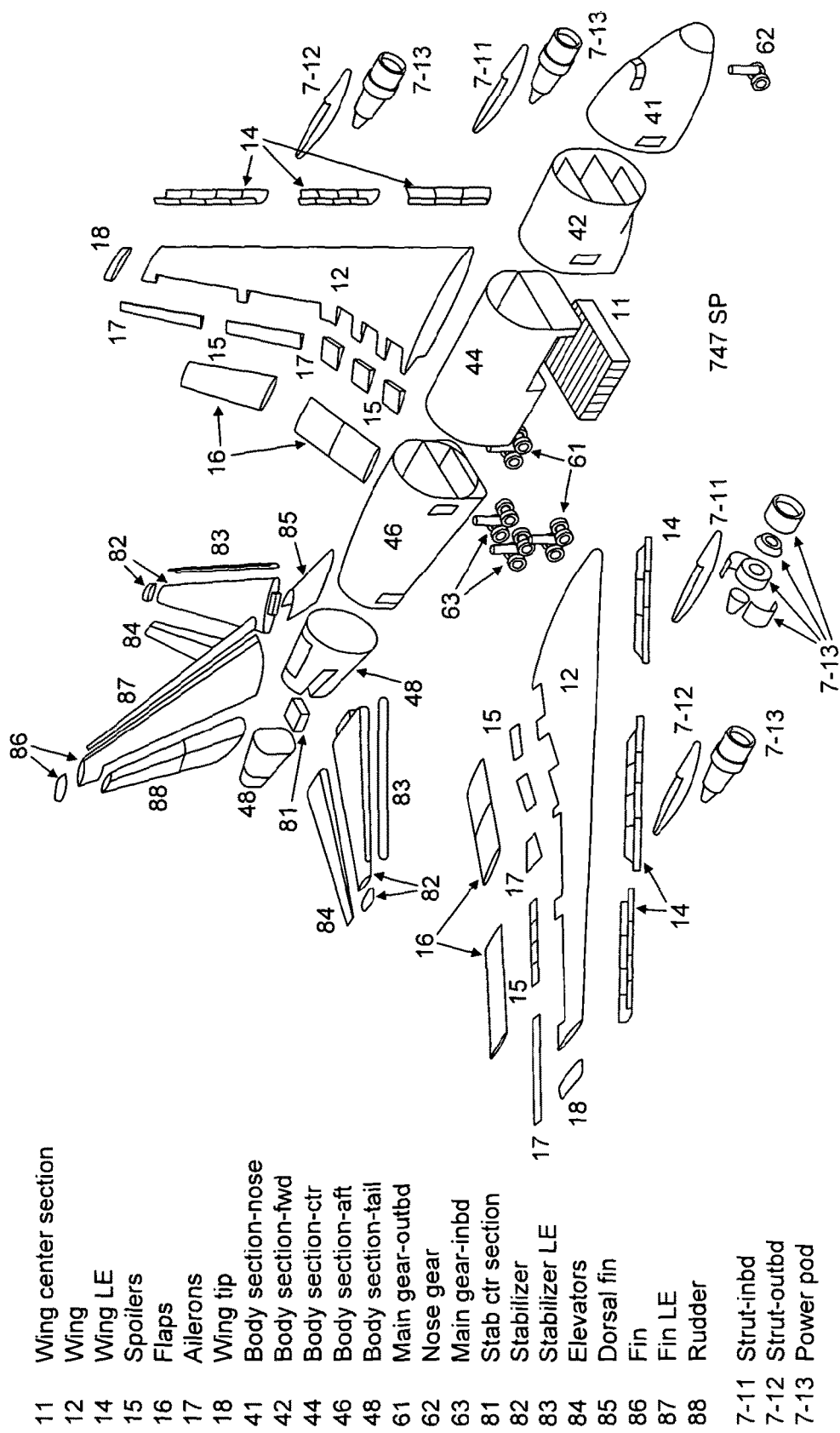
Figure 13B:
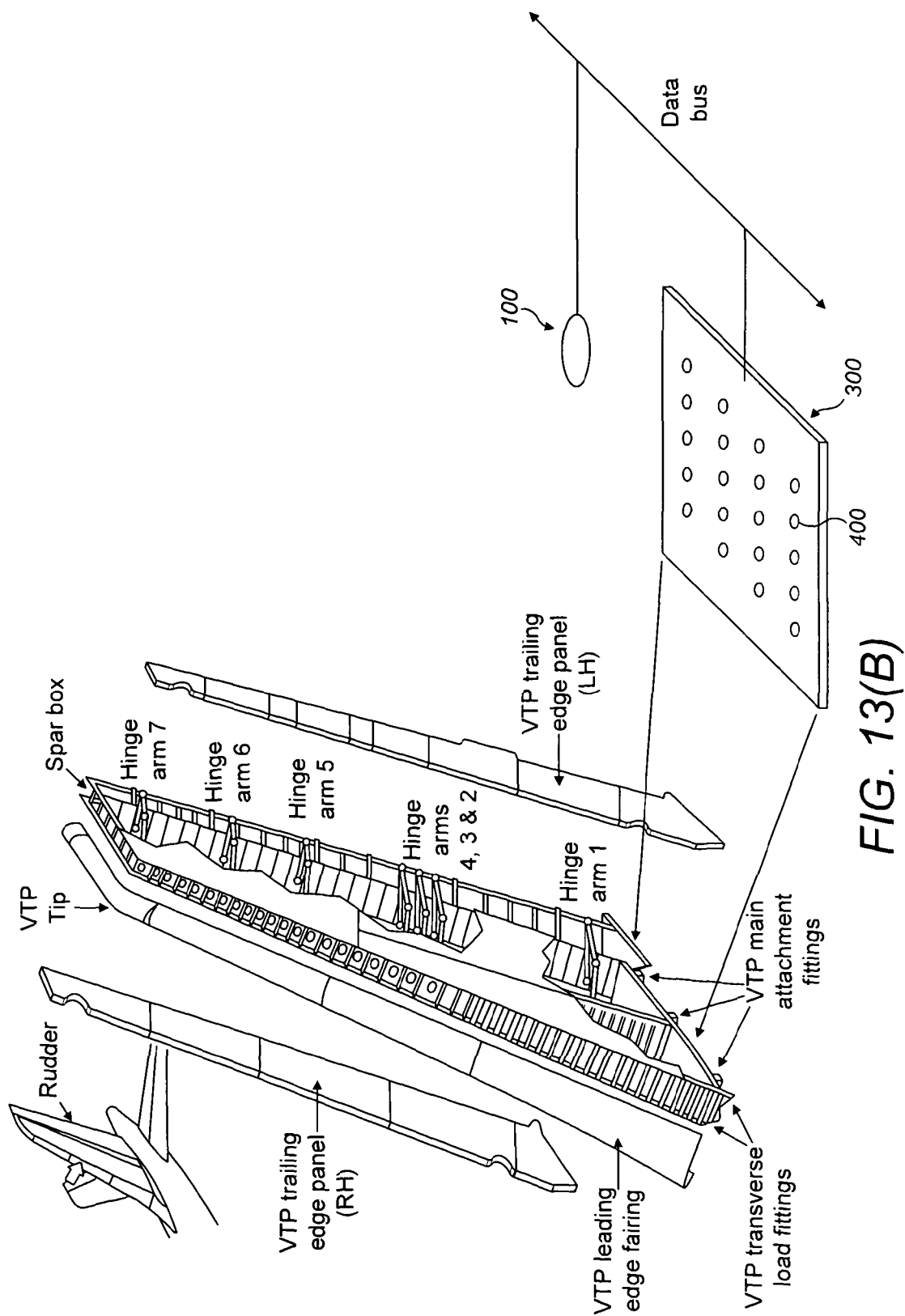
Figure 14:
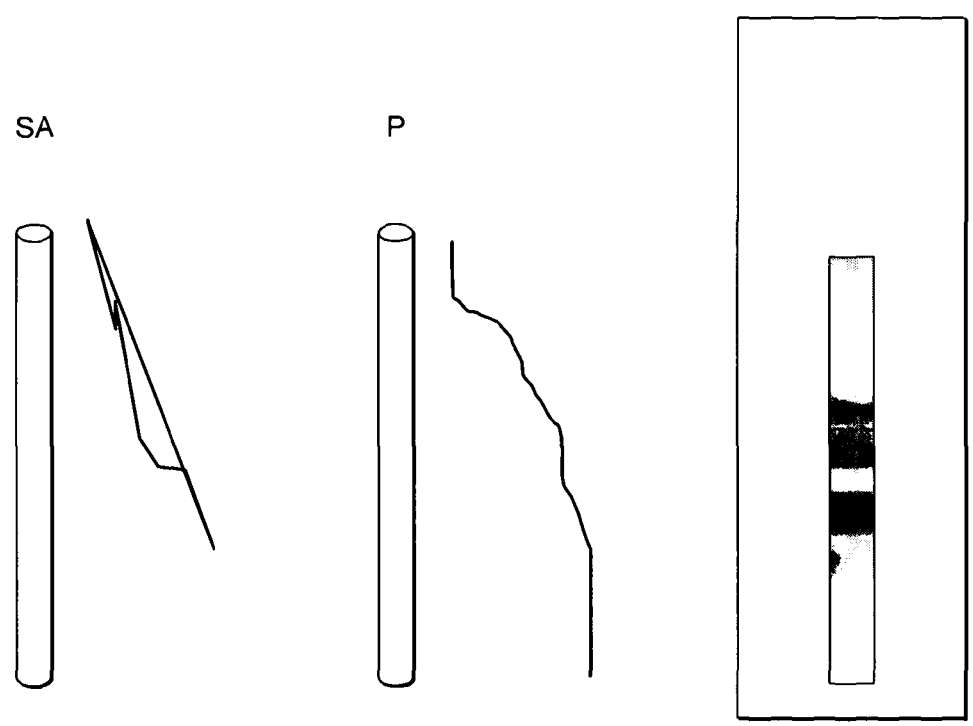
Figure 16:
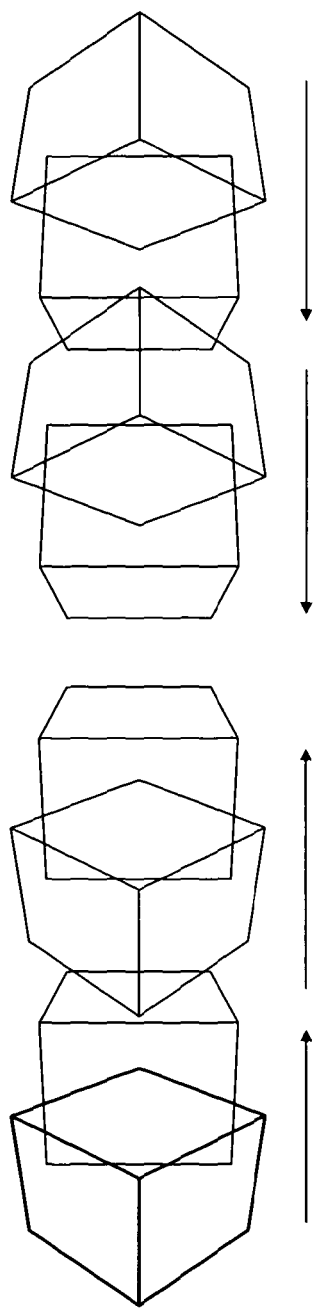
Figure 17:
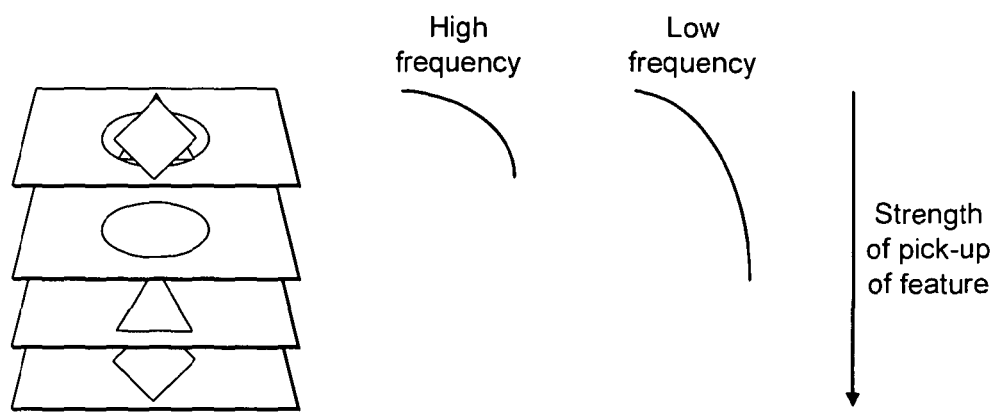

FIGS. 3(A) and 3(C) show examples of outputs obtained when employing a system according to the invention;

FIGS. 3(B) and 3(D) show examples of outputs obtained when employing a material having a disordered particle lattice; FIGS. 4(A) to 4(D) schematically show radio detection geometries according to the present invention;

FIGS. 5(A) and 5(B) schematically show methods for introducing a radio signal into a composite 'cell';

FIGS. 6(A) and 6(B) schematically show methods for coupling composite 'cells';

FIGS. 7(A) to 7(C) show detection methods from probe elements;

FIGS. 8(A) to 8(C) show high impedance probes;

FIG. 9(A) schematically shows an example of signal detection;

FIG. 9(B) illustrates a surface array of active antenna probes scanning a composite cell;

FIGS. 9(C) to 9(E) show three circuit variants for transmitting the information collected as shown in FIG. 9(B) to a receiver;

FIG. 10 schematically shows a detection method using a synchronous receiver;

FIG. 11 schematically shows a detection method using a network analyser;

FIG. 12 shows representative images of composites obtained using a method according to the present invention;

FIG. 13(A) shows a list of airliner parts that are likely to be made from composite materials;

FIG. 13(B) schematically represents a testing scenario using a method according to the present invention;

FIG. 14 shows the detected distorted field of a non-uniform rubber composite material;

FIG. 15(A) to 15(C) show processes of data management;

FIG. 16 represents a Yeecell method;

FIG. 17 represents a method of building 3D image of a composite; and

Figure 18:
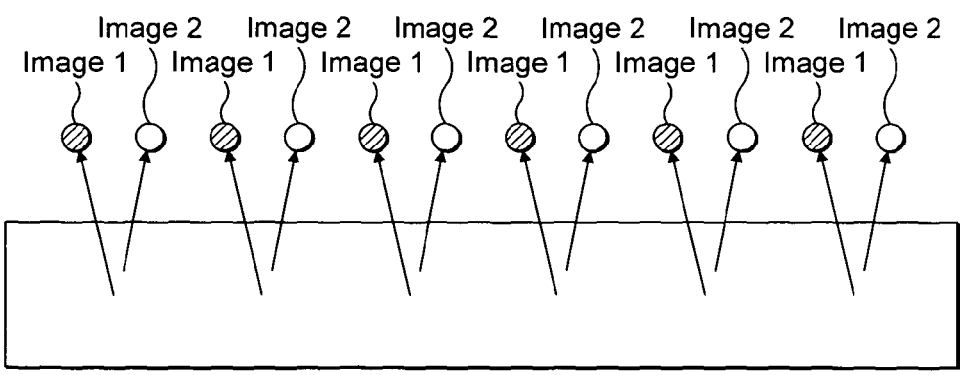

FIG. 18 represents a stereoscopic imaging method.

Figure 1:
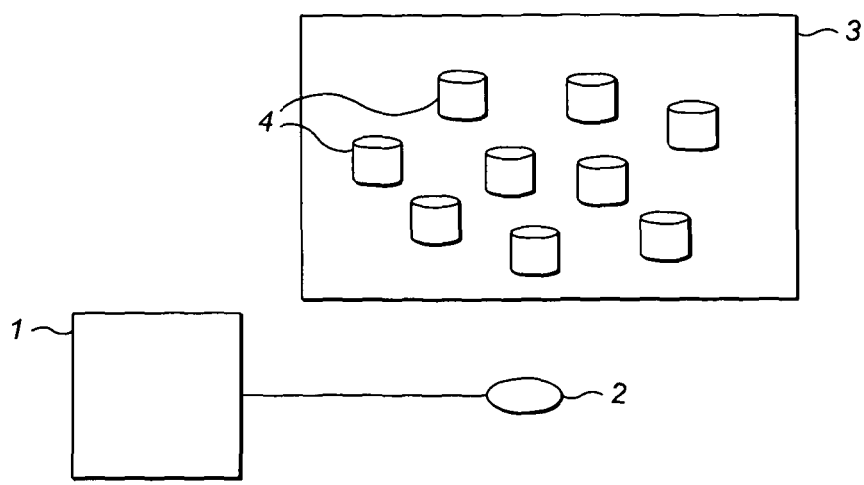
FIG. 1 is a schematic diagram of an example of a prior art intrinsic sensor.

Referring to FIG. 1, a schematic diagram of a wireless transceiver 1 having an antenna 2 is shown. A portion of material 3, for example a polymer material, has a matrix structure in which multiple sensing elements 4 are embedded such that the sensing elements 4 are dispersed within and surrounded by the matrix material 3. The sensing elements 4 have electron distribution and/or transport properties that change in response to a change in a physical or chemical property of the material. This behaviour results in an alteration in a radio frequency (RF) signal (for example, a microwave signal) that is transmitted from the transceiver 1, via the antenna 2, to interrogate the matrix material 3, such that the change in the material can be determined from the received signal. In this way, the sensing elements 4 allow non-invasive, intrinsic sensing of a change in the properties of the material.

Accordingly, the prior art intrinsic sensor of FIG. 1 uses the microwave resonance of embedded sensing elements 4 in order to link the radio properties of the composite material to its structure.

Figure 2:
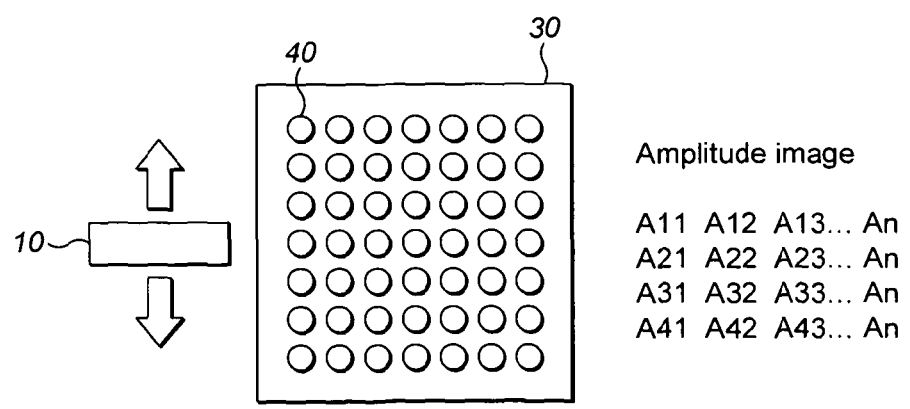
FIG. 2 is a schematic diagram of a system according to the invention.

FIG. 2 shows an example of an intrinsic sensor according to the present invention. A basic radio probe 10 for detecting radio signal amplitude is shown. Preferably, the radio probe is an open ended coaxial line which has a concentrated field. A portion of material 30, preferably an insulating polymer material, has a matrix structure comprising particles (or fibres) 40, preferably conductive particles. Unlike the prior art sensing elements 4 of FIG. 1, conductive particles 40 do not have microwave resonance; conductive particles 40 are purely reflective. The conductive particles 40 are equally spaced within the matrix material 30 such that they form an ordered lattice-like structure. The composite material therefore has essentially a quasi-crystal form.

In fabricating the composite material, it is important that the conductive particles 40 are substantially equally spaced within the insulating material 30. Particles 40 that can be used for this purpose may be spherical, or may consist of fibres, sheets and other shapes. It will be understood that a wide variety of particles 40 may be used such as metallic plates, graphenes, aluminium, silver, copper or gold particles. Alternatively, particles 40 may include semiconductors (organic and inorganic) and conductive polymers. Furthermore, carbon black material (which exhibits an ultra uniform particle distribution) or carbon fibre, such as carbon fibre sheets may be used.

The key property of the material 30 of the present invention is that the distance between particles 40 is regular, so that the material forms a lattice-type structure. The structure is almost similar to a quasi crystal, although it will be appreciated by the skilled person that any matrix material 30 wherein the distance between the particles 40 is regular in at least one dimension may be used. It is also important that the particles 40 are non-insulating, so that there is coherent periodicity in an electrical property of the composite material known in the art, such as periodic conductivity or periodic dielectric constant. Preferably, the particles 40 are conductive, although it will be appreciated by the skilled person that any non-insulating particles may be used, including semiconducting particles. Preferably, the matrix is non-conductive, such as an insulator, to achieve a conductor-insulator-conductor-insulator periodicity. The electrical periodicity is required in at least one spatial dimension. Therefore this periodicity may be in 1, 2, or 3 dimensions (ie 1D, 2D, or 3D).

A mechanism that uses radio waves to interrogate this quasi-crystalline composite material is described below.

If the conductivity and/or size of the particles 40 is low, radio signals will penetrate the composite material. For some materials, this penetration may be several centimeters in the MHz-GHz range. In contrast, in metals and conductors, radio waves penetrate to only the skin depth, several microns. The composite material used by the present invention allows a radio signal to penetrate it, for several millimeters to centimeters, so that the returned signal relates to the composite structure.

The radio signal reflects from each particle 40, each particle acting much like a mirror to the radio signal. However a significant part of the radio signal penetrates deeper into the probed material, being reflected by several particles 40, so that, at the surface, a net reflected signal may be detected. Therefore the net reflected signal is related to the volume of the composite material being probed and the depth of the probed composite material depends on how far the radio signal penetrates. As this depth is a small fraction of the wavelength, phase and interference effects at the surface, where the signal is detected, are negligible. Therefore, to a first approximation, only the amplitude of the detected signal needs to be measured.

Thus, the change in the returned signal is preferably detected as a change in the amplitude of the returned signal, although it will be appreciated that there are also slight changes in the wavelength, phase and interference of the returned signal, which relates to measuring composite charge.

The method according to the present invention, if needed, can use much larger signals than the method associated with the prior art intrinsic sensor of FIG. 1, making the present invention suitable for a larger range of applications without optimisation.

Therefore the composite material according to the invention acts like a 3D mirror to microwaves wherein the reflective properties of the mirror can be affected by damage to the composite material. The reflected radio signal can detect a change in a property of the material, for example a fault type such as subsurface cracks in the composite material.

Accordingly, the present intrinsic sensor uses a 'volume' reflectivity (rather than the microwave resonance of the prior art sensing elements 4 of FIG. 1) that is constant across the composite material in order to link the radio properties of the composite material to its structure. It will be appreciated however that in some instances reflectivity may vary with position that would be changed by damage according to a known function.

The radio transceiver 10 is constructed to generate and transmit a radio frequency signal and to detect the transmitted signal and a returned signal from the composite material in real-time. The net reflected radio signal is at various locations across the material typically collected via a scatter, reflection, or transmission set-up (reflection being likely for most applications). As explained above, the tracked amplitude of the net reflected signal is linked to the environment of the conductive particles 40. The net result of damage to the composite material is a change in the returned signal's amplitude compared to the surrounding material thereby providing remote collection of information about the physical and chemical properties of the bulk composite material. The measurements of the transmitted and returned signals may take place at the same location, or, alternatively, one may track changes in traveling modes that propagate through the composite material.

Figure 3:
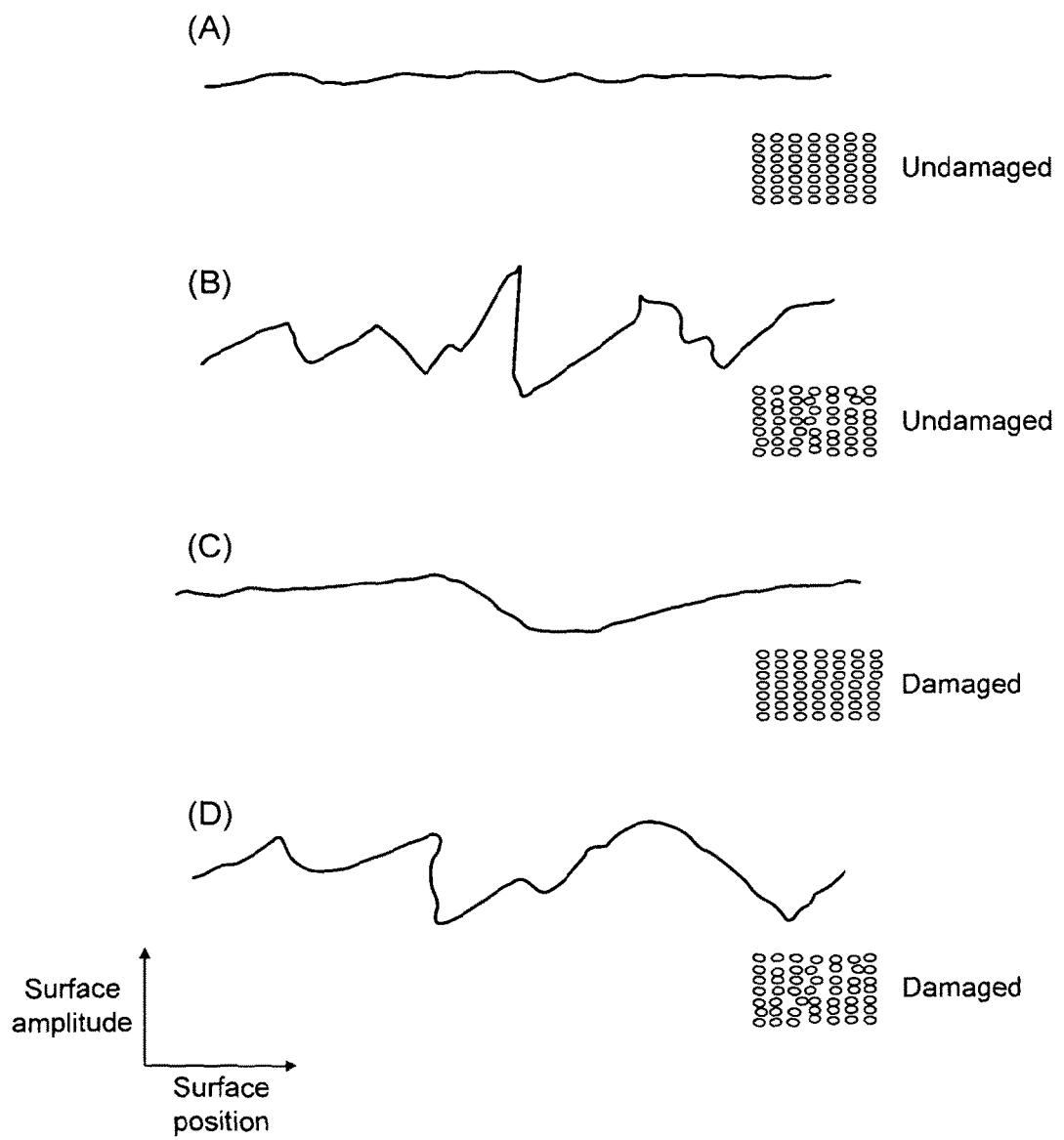

FIG. 3(A) shows the smooth surface returned signal amplitude seen at the surface of a conductive particle lattice material as described above, while FIG. 3(B) shows the rough surface amplitude for a disordered (and undamaged) particle lattice. FIG. 3(C) shows how an internal crack in the material of FIG. 3(A) is obvious after damage. FIG. 3(D) shows how, in contrast, an internal crack is not obvious for the disordered lattice of FIG. 3(*b*). If the spacing between the particles 40 changes, for example through damage, the impedance inside the material 30 will change. Hence the surface radio impedance/potential will also vary in a related way. It also means that there is varying penetration of the radio signal into the composite material, that is a varying skin depth.

A conventional mirror must be very smooth so that when cracks occur, they are obvious against the smooth background. Likewise, for the 3D mirror to reveal cracks, it must be smooth to radio waves. This smoothness may be achieved by spacing the particles 40 evenly within the insulating material 30.

Processes may be developed to make the composite material 'radio smooth'. These include processes to adjust conductivity to allow radio penetration (at the chosen operating frequency) or to tailor the dielectric properties of the composite material and optionally add thin conductive coatings to guide traveling waves such that the composite material itself converts or transduces the mechanical damage so that it is visible in a reflected radio signal. Therefore the material used in a system according to the present invention may be regarded as an intrinsic sensor.

Apart from conductivity differences between the conductive particles 40 and the insulating material 30, dielectric differences can also be used to create a 3D reflector, so long as sufficient radio penetration into the composite material is possible. Conductive and dielectric differences can be viewed more generally as using the electronic differences between two materials according to their atomic structure. This includes conduction or polarisability of band structure. In some applications it may be possible to dope a contiguous or non-contiguous semiconductor material to create an electrical periodicity.

This damage-detection technique is very sensitive to spatial changes within the quasi-crystal. Such changes represent positional changes of the particles 40 away from regular order which may be caused by damage. Furthermore, temperature, strain, vibration and chemical change may also alter the position of the particles 40, however detecting these parameters requires the development of correlation models and software. The insulating matrix 30 can be then adapted to optimise its sensitivity to these parameters. For example a soft polymer material 30 will expand and contract more easily, so it is more sensitive to temperature.

Figure 4:
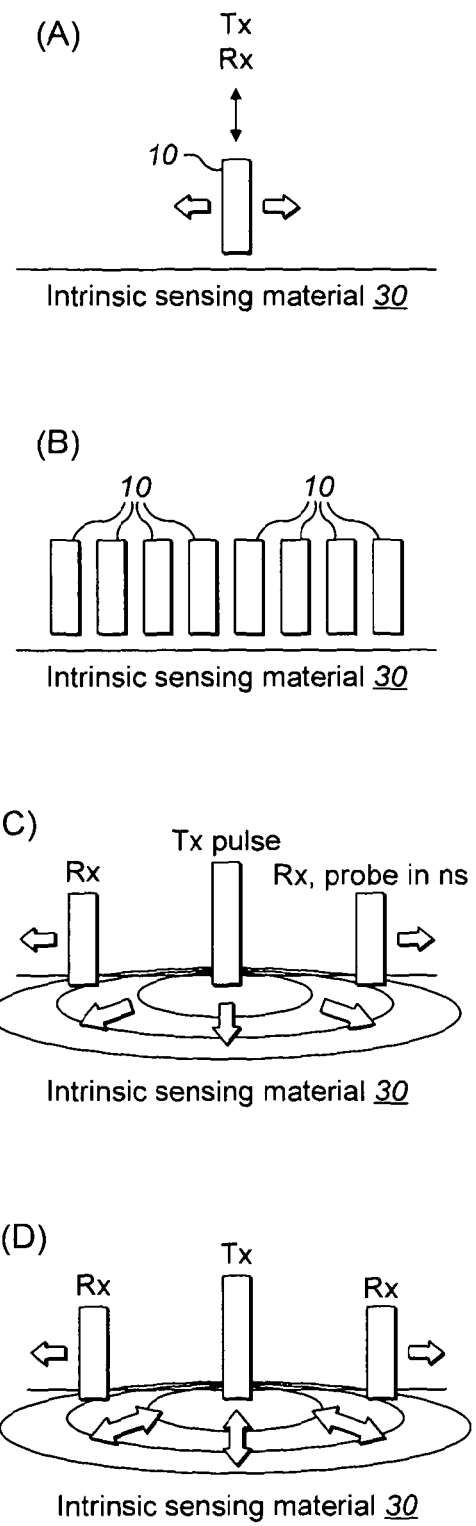

FIG. 4 schematically shows methods for local wave and travelling wave measurement according to the present invention. The operating principle is based on the fact that composite plates are partially conducting and have dielectric properties that allow interrogation via travelling waves propagating through them. To achieve this in practice, one may couple a transmitter Tx via a proximal antenna and matching units known in the art to instigate a propagating wave mode.

A lateral wave propagates largely in two dimensions from the antenna source. This may be also regarded as a leaky wave due to the attenuating nature of the medium, which has the advantage of reducing interference from boundary reflections that normally create standing waves. The leaky wave is an electromagnetic wave attenuated by the composite medium, while attenuation helps to reduce unwanted reflections.

With reference to FIG. 4(A), an open-ended coaxial probe 10 can transmit a radio signal via a transmitter Tx and detect via a receiver Rx the returned signal (surface potential, impedance, voltage etc) at a specific point located at coordinates XY. Receiver Rx may comprise an antenna. Collecting evanescent signals at multiple points enables the creation of an image. This can be done, for example, by scanning mechanically or by forming a coaxial probe array (represented in FIG. 4B) as known in the art. The coaxial probe array uses a bank of electronic switches instead of mechanical scanning, giving significant practical advantages in terms of speed and reproducibility. Accordingly, the detection mechanism involves measuring the field amplitude across the composite component, which effectively acts as an antenna itself. However, in the case relative to an almost perfect component, dielectric boundaries and discontinuities of wave impedance due to composite damage alter the signal amplitude, which in turn, are detected in the image.

With reference to FIGS. 4(C) and 4(D), analysis of a composite material 30 is conducted according to the present invention by treating the probed region of the composite as an antenna element that is anisotropic. Radio waves transmitted from the transmitter Tx travel with a circular wavefront. The probed composite region or structure in which the RF signal travels and which may be regarded as an antenna element is also referred to as a 'cell'.

A transmitter Tx may be attached to the structure or cell by capacitive coupling. The transmitter Tx represents a RF source which introduces an electromagnetic EM field mode within the material 30 and this mode couples to the surface evanescent field of the material 30. Accordingly, the surface evanescent field may be probed with the receiver Rx.

The composite material 30 is then probed at various points from the centre of the radio disturbance. This field mode can be a continuous wave involving cell edge reflections, detected by scanning node and antinode positions as shown in FIG. 4D. Alternatively, the field mode may be a traveling wave, detected by scanning the amplitude of a leaky wave mode that decays toward the cell boundaries. In rare cases, if total isolation of a volume is needed, it is possible to use, a pulsed radio signal to avoid reflections from the boundaries of the structure or cell (FIG. 4C). In this format damage will perturb the composite material 30 and there will be discontinuities and variations in wave speed that will alter the distribution and strength of the evanescent electric field (i.e. the 'texture' of the evanescent electric field) to reveal sub-surface information. The 'texture' of the evanescent field relates to the crystallinity of the composite material and can be used as a gauge of composite quality.

Accordingly, the volume of the region of composite material scanned may be established by electrical addressing the transmitter source of the cell or modulating the radio signal with a specific signature or tag, using known digital and analogue techniques, to flag that the radio signal came from this particular transmitter source. The volume scanned relates, in most cases, to the area of a component of the scanned composite material. For example, in the case of panels forming a skin, each panel represents a cell. The cell boundaries may be determined for example by establishing whether the strength of the tagged source is above a certain threshold. In certain cases, it may be possible to reduce cross talk present between the cells by time-gating methods commonly used in mobile phone networks.

To ensure efficient transmission through all components of the scanned structure, attention to the plate thickness, operating frequency and the dielectric constant is needed. To detect the travelling wave, antenna receiving probes Rx are placed on the top side or the underside of the composite panel, the former appropriate for on-site maintenance, the latter for real-time monitoring at critical points of the material, such as for example, critical points in an aircraft.

The composite may be provided with a thin metal coating. This may help to form a waveguide for the travelling wave, however one would have to probe from the opposite side if the coating is very thick.

Using the different methods of FIG. 4 helps to best accommodate measurement scenarios where shape and material (electromagnetic impedance) cannot be changed.

Resolution depends on probe dimensions (mm sized) and separation rather than frequency. GHz frequencies may be used, however, since penetration is inversely related to frequency, frequencies may also be reduced to the MHz region to increase penetration into the structure.

The intrinsic sensor according to the present invention may be calibrated. Sensor calibration relates to the collection of the raw signal, and its time stability. Hence aspects relating to calibration involve, principally, the drift of the antenna probe system due to temperature. By measuring temperature along with the evanescent field, a calibration offset can be incorporated into the data processing algorithm.

The variation in the surface signal may be used to generate a 2D colour map. It will be appreciated that scanning at multiple frequencies may lead to a series of different 2D maps containing information from different depths. This data can be processed to make a 3D image. Therefore, both the 2D and the 3D maps visually represent the damage.

Figure 5:
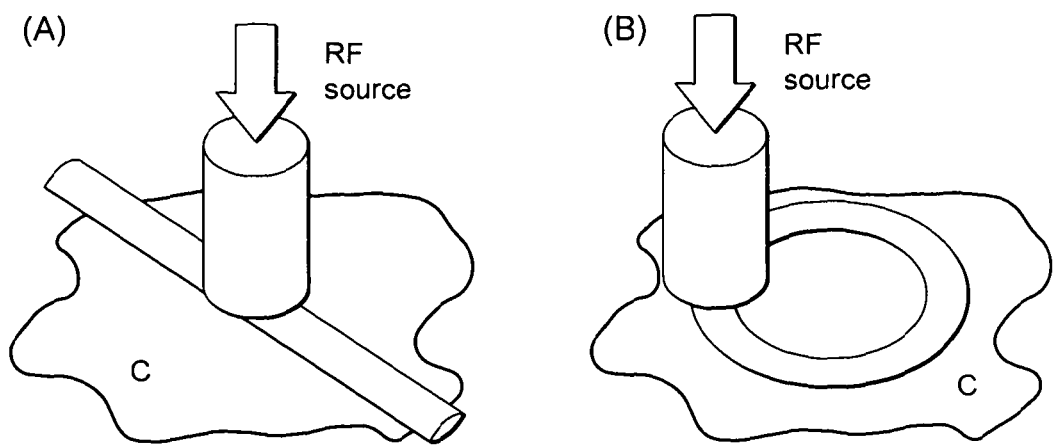

FIG. 5 shows methods for introducing input radio frequency signals (represented by arrows) from one RF source into a composite cell C. As explained above, each cell is regarded to act as an antenna element. Excitation of the antenna element may be via a dipole as shown in FIG. 5(A) or a ring antenna as shown in FIG. 5(B), for example. It will be appreciated that, in practice, the antenna element will be a more complex radiating component depending on the properties and shape of the composite material. However, a smooth variation of the evanescent field with position is retained if the scanned composite material is not damaged.

The RF source introduced an electromagnetic field within the composite material which couples to the surface evanescent field of the composite which may then be probed with a surface field probe array, for example. Accordingly, it is the surface evanescent field that is of interest rather than the far field that most antenna manufacturers usually aim to improve.

By treating each cell as an antenna element, it is possible to 'fix' the input RF signal in each cell. Each cell acting as an antenna element may be excited by one RF source or a plurality of RF sources may be used to excite one cell.

FIG. 6(A) schematically represents methods for feeding a radio signal to a plurality of different cells C of a composite structure when there is only one RF source available. A plurality of cells forms an 'array' of cells. The cells may be coupled in order to pass the returned signal collected from each probe array to a suitable collection point for storage and/or further processing. A suitable collection point or hub would be decided by the constraints of the scanned structure.

Within each array, the cells C may be coupled by a wiring 'loom' WL which may comprise for example optical fibre, wire or any other structure which allows data to be collected from the cells C. Alternatively, the data from the cells C may be coupled via induced modulated RF currents passing through partially conductive cells C, as represented in FIG. 6(B).

Figure 6:
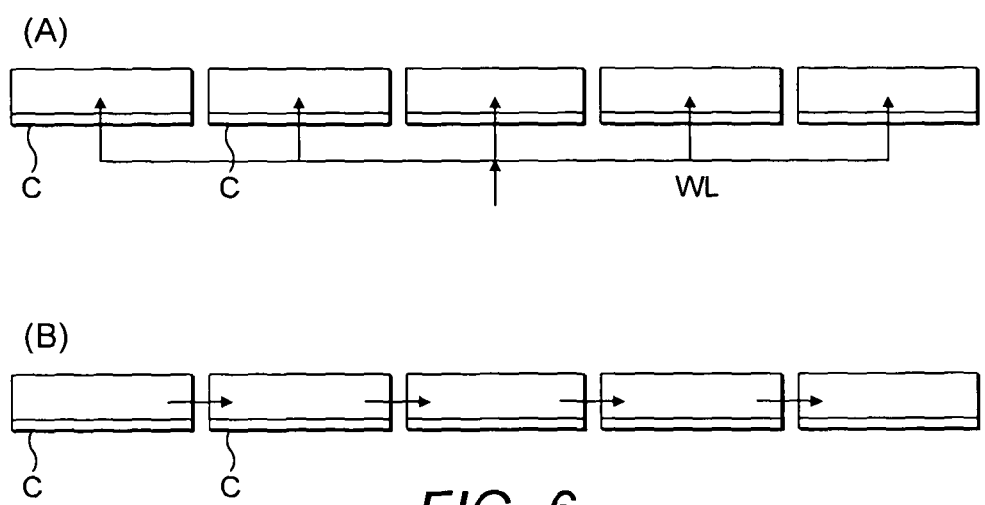

According to the methods for coupling a plurality of cells as shown in FIG. 6, a single RF source may be used to illuminate an array of cells. Advantageously, these methods may be used to overcome practical constraints during scanning of composite panels, for example, when the composite material is part of a larger structure and the RF source cannot be placed in practice inside the larger structure. Another major advantage of scanning cell arrays (or a cell network comprising several cell arrays) is reduced scanning time and the possibility of real-time scanning. In the case of manufacturing an aerospace structure, for example, it is preferable to apply probes in a sheet like form when the aerospace structure is close to completion.

Accordingly, the probe array may be integrated into a test structure wherein the probe array must be placed proximal to the test material. During a simple composite material sample testing for example, the probe array can be external and on the top surface of the composite material. The monitoring of the structure, such as an aircraft, can also be performed by external placement of the probe array in the suspect area. However, preferably, the probe array is loaded on an inner surface, and integrated into the structure as a centre sheet. In this way the probe array becomes an integrated field measuring and transmitting device for accessing the evanescent field of the composite material below it. It is envisaged that this centre sheet may also be part of the material itself, when used for testing next-generation materials that have their own 'nervous system'.

Figure 7:
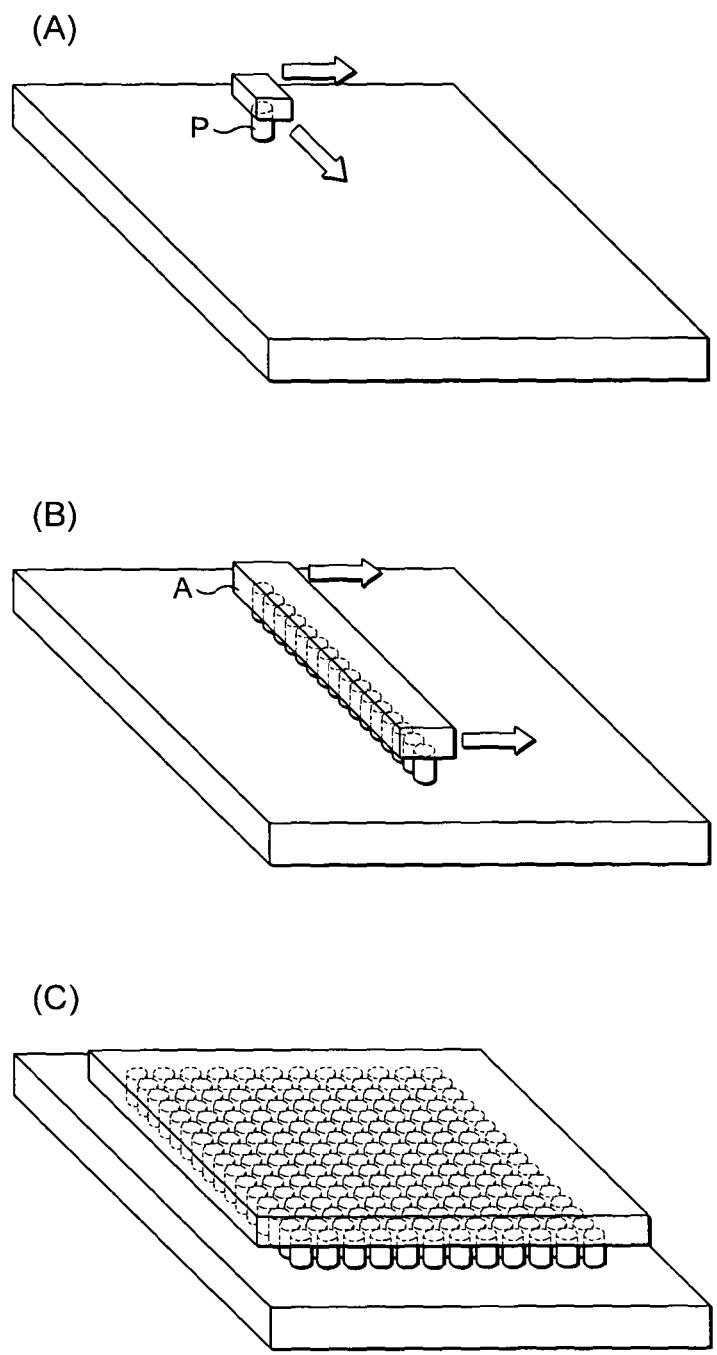

FIG. 7 shows different methods for receiving signals from composite materials. The probes P in FIG. 7 may be, for example, co-axial probes that function both as a probe and a source. Alternatively, the probes P may be high impedance probes of the type described below with reference to FIG. 8.

In FIG. 7(A), a single probe P comprising a single antenna may be mechanically stepped over the area of the composite material. For example, this receiver is suited for scanning individual panels, which are easily accessible and do not necessarily form part of a larger structure.

A 1D probe array A with electronic switching as shown in FIG. 7(B) may be moved in one direction along the composite material. For example, the 1D probe array A comprising a plurality of probes P may be advantageously swiped across a panel forming part of a structure or may be used to test an isolated, individual panel.

FIG. 3(C) shows a 2D probe array with electronic switching between antennas in the probes. Alternatively, the 2D probe array may have multiple signal channels. The 2D antenna array is suited for both scanning individual panels or panels within a structure, however this type of receiver is preferably used to scan cell arrays, wherein the array may form a cellular network within the structure. The plurality of cells can be built to correspond to a wireless cellular network or mesh network that can act as a composite 'nervous system'. The 2D antenna may be used for multi-channel photography (to create 2D or 3D colour maps as explained above).

Figure 8:
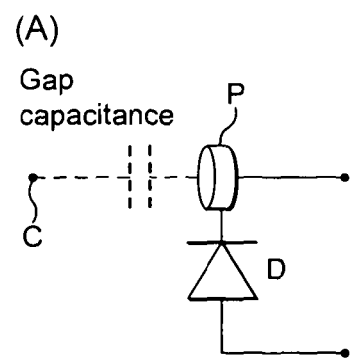
Figure 8:
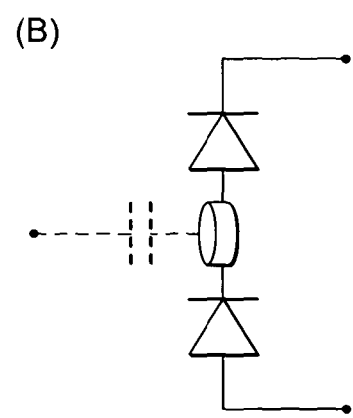
Figure 8:
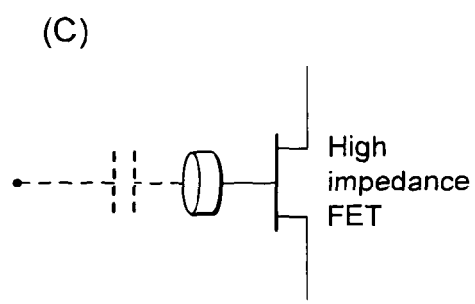

FIG. 8 shows individual antennas which may be used in the antenna arrays represented in FIG. 7(B) or 7(C). The antennas of FIG. 8 represent high impedance probes which are well suited for a homodyne or similar receiving system, to measure the amplitude of this signal, or its harmonic.

It will be appreciated that the high impedance probes may be used in any receiving system known in the art, including both heterodyne and homodyne systems. However, homodyne systems have a higher performance in cases where there is relatively high ambient noise. Homodyne systems are suited particularly when there is direct access to the source. In a homodyne system, the source signal and the received signal are mixed to obtain an almost DC level signal which contains the required information (in this case, the local evanescent field). Advantageously, the noise level obtained from any other signals at a slightly different frequency averages to zero. Accordingly, homodyne receiving systems provide extremely narrow signal filtering, typically less than 0.1 Hz.

It is noted that the high impedance probes P of FIG. 8 may only function as probes and not as sources. The high impedance probes are also known as voltage based antennas or active antennas and provide the advantage that they can operate over very wide bandwidths and can be extremely compact, up to several orders of magnitude smaller than their electromagnetic wavelength.

FIGS. 8(A) to (C) show connections between a composite surface point C and active probes P. The active probes P may be used to scan relatively small areas of the composite, for example in the millimeters range, and are therefore referred to as small area probes P. The small area probes P may form the elements of an array of high impedance probes. The probes P are spaced from the surface of the composite by a gap. Accordingly, small area probes P couple capacitively to the local surface evanescent field of the composite.

Provided that the small area probes P are in a high impedance region and that they do not contain too much metal such that they distort the evanescent field, the charge which may be accumulated with the probes P may be a faithful reproduction of the strength of the evanescent field in that composite region. In preferred configurations, the high impedance probes may be made from relatively small metal elements spaced from each other or micro-elements referred to as metal 'dots' or 'spots', in order to avoid perturbing the evanescent field. Alternatively, the metal elements may be a small wire loop.

FIGS. 8(B) and 8(C) show high impedance probes which comprise RF signal diode rectifiers D in order to rectify the detected signal. Preferably, the diodes are germanium diodes such that a DC voltage may be detected, which, from does not capacitively couple to neighbouring lines, as shown in FIGS. 8(B) and 8(C). To avoid the diode leaking charge from the active probe, and therefore reduce its voltage, the gate of a field effect transistor such as a high impedance JFET can be connected to that probe instead, as shown in FIG. 8(D). Depending on the noise level of the measurement, this signal voltage may include contributions from other unwanted sources. In this case, the probe shown in FIG. 8(D) may comprise an additional signal mixing section (not shown) so that it is multiplied with the source frequency. Therefore, on this basis, the probe of FIG. 8(D) may detect signal components only at the source frequency, all other frequencies averaging to zero.

As an alternative to the high impedance probe of FIG. 8, a co-axial probe of the type described above may be used in a network analyser.

FIG. 9(A) shows an RF source of the type described in FIG. 5 which introduces an electromagnetic EM field within a composite material 30. Accordingly, the introduced EM field constitutes an electromagnetic mode within the composite material 30. In turn, the electromagnetic mode couples to the evanescent surface field of the composite, which may then be probed with a surface field probe array A, of the type described in FIG. 7(B). The measured electrical potential or voltage at a scanned surface point is preferably measured with a high impedance probe (of the type shown in FIG. 8). In many cases, the electric potential or voltage is proportional to the surface impedance which represents the ratio of the electric and magnetic components at that point. A network analyser can also obtain the surface impedance by measuring the phase an amplitude of the power reflected back from a co-axial probe at that point.

FIG. 9(B) shows an array of active antenna probe array A, probing the surface of a composite cell C spaced from the array by a gap. Data from the probe array is collected in a common collection point for the cell C, also referred to as a cell hub H. The surface evanescent field measured by the probes forms in a region which may be stabilised by a spacer (not shown). Preferably, the metal content of the probes is as little as possible, in order to avoid the loading and distortion of the surface evanescent field. Accordingly, electrodes of each antenna probe (and therefore the electric charge stored on the electrodes) are preferably accessed by a conductor having a very short length. The short length conductor may feed into a high impedance buffer of any of the type shown in FIG. 9(C) for example. Beyond this point in the circuit (the buffer), the sensitivity to surface fields is much reduced due to the lowered line impedance as well as screening of the co-axial line.

FIGS. 9(C) to 9(E) show three circuits suitable for gathering information from a probe array A to feed into a cell hub H. Each of the three circuits transmit information about the strength of the evanescent field detected by the active antenna probe array A (shown in FIG. 9B). The first circuit shown in FIG. 9(C) uses a low-pass filter F which allows to pass an almost DC level signal along a thin co-axial line (micro co-axial cable MC) to a receiver.

The second circuit shown in FIG. 9(D) comprises a voltage to frequency converter VFC instead of the low-pass filter of FIG. 9(C). Converting the voltage to a high frequency at the point of detection preserves the information better when the signal is transmitted for example through a noisy transmission region. In some cases, an analogue to digital converter may be used instead.

The third circuit shown in FIG. 9(E) is also intended for potentially noisy environments. The circuit comprises a voltage to frequency converter VFC and an optical modulator OM, for example a light-emitting diode, which may transmit the signal to a receiver (now shown) via an optical fibre OF. Advantageously, this circuit is immune to electrical noise and insures high quality data is received at the cell hub.

FIG. 10 shows a method for electrically capturing the surface evanescent field of a composite panel without 'loading' the field with a conductor (if the field is 'loaded', it is distorted and its strength is effectively reduced by the presence of the conductor). This method can faithfully capture the profile of the evanescent field from either the upper or the lower side of the panel. A synchronous (homodyne) receiver is used to provide extremely narrow band filtering (typically, less than 0.1 Hz) of small radio-frequency signals as a function of position by virtue of electronic switching which connects each of the individual probes (p1, p2, . . . pN) to the receiver in a defined sequence. The probes may be high impedance probes of the type shown in FIG. 8.

FIG. 11 shows a detection method using a network analyser for detecting the electric field at the probe (p1, p2, . . . pN), which is typically a co-axial probe. The RF source may be incorporated within each probe (p1, p2, . . . pN) and the probe impedance may be measured to obtain, in turn, the surface impedance of the composite. The co-axial probe may be an open co-axial line, wherein signals are both transmitted and received from an endpoint of the co-axial line. The charge on the endpoint of the co-axial line may change due to differences in the evanescent field. The network analyser may be configured to detect changes in amplitude and phase of the received signal. The change in charge may also be converted into a change in field impedance represented by the ratio of the electric and magnetic components and/or loss tangent.

FIG. 12 shows representative images of composite panels used for detecting damage in composite panels via intrinsic sensing. A radio geometry employing a co-axial probe array (as represented in FIG. 4 (B)) was used in this application. FIG. 13(A) shows a list of airliner parts that are likely to be made from composite materials, while FIG. 13(B) represents a testing scenario wherein the root region of an airliner tailfin is investigated for fatigue damage. Fatigue damage also known as 'buffering' can arise in this region due to oscillatory stresses and strains at the rear of the aircraft. This makes desirable continuous monitoring of this region, which may be achieved using the method according to the present invention.

In this scenario, a semi-flexible sheet 300 may be fixed at the root region before or after the assembly. Furthermore, the probes can be incorporated into a flexible antenna/probe sheet that may use flexible electronic technology. Field sensing devices 400 are used for scanning the topography of the region while an RF source 100 is used to excite low frequency EM modes in accordance to the present invention.

FIG. 14 shows the detected distorted field of a non-uniform rubber composite material detected using the methods described above. As explained above, distortions in the surface evanescent field may be obtained with a 'wire' antenna or probe P of the type described in FIGS. 8 and 9. The distorted electric field contains information about any defects present in the material. In contrast, the surface evanescent field detected with a standard wire antenna SA is smooth and therefore does not reveal the defect in the material.

During measurements of large composite material structures, a control centre may be used to detect a data acquisition event occurring at a specific cell address. This triggers the data acquisition process. When this happens, a source RF signal is generated in the relevant cell. This signal is transmitted throughout (i.e. permeates), the composite material structure. The signal may be enhanced by any layered conductive/insulating regions of the structure. The signal is reflected throughout the material, creating in the simplest approximation, a 'shadow' of the composite's spatial conductivity. At the surface, this information is in the evanescent wave that is detected by the probe in as a voltage signal. A heterodyne or homodyne method may be then used to measure the amplitude of this signal, or its harmonic.

Figure 15:
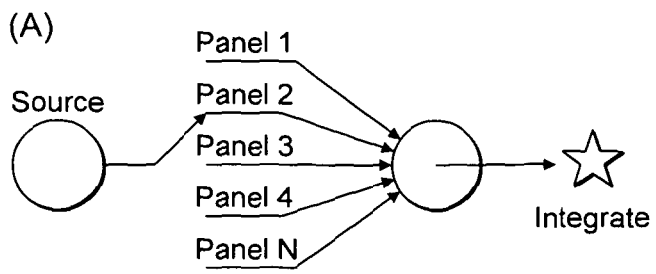
Figure 15:
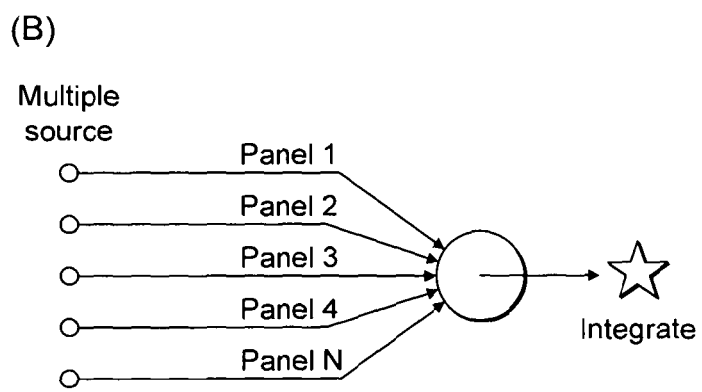
Figure 15:
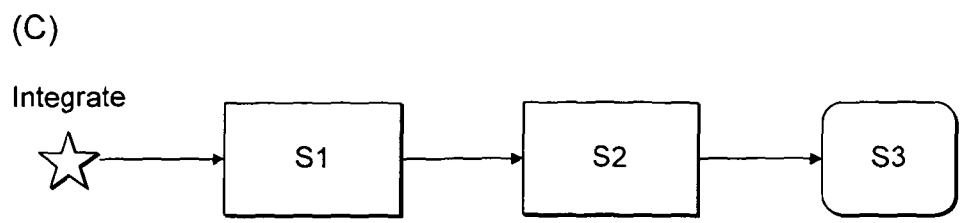

FIG. 15 represents the collection of structural health data from a large composite structure formed of multiple panels. A number of composite cells may be scanned in accordance with the methods described above. The cells may be scanned with a number of array probes that are associated with a single source within the cell, or, alternatively, are associated with multiple illuminating sources within the cell. By including a switching means and receiving system within the cell it is possible to collect an integrated set of raw data expressing the electromagnetic field as a function of position for the whole composite structure. The data is then integrated at a central point. The data may then be stored (S1), processed (S2) and an image data may be obtained (S3). Alternatively, data processing may be done off line if feedback is not required immediately.

Once the data has been collected from a network of individual cells, it can then integrated into as a raw data set that represents the evanescent field of the entire structure. The first processing step is restoration by reducing noise and any motion blur using a selection of filters such as Bayesian filter known in the art.

The next processing step is to recognise a geometric object that has a specific feature. To extract features for specific types of damage, the percent inventors train algorithms, using an established library of evanescent field textures determined numerically and experimentally from the composite pseudo-crystal structure. These evanescent field textures have unique spatial frequency components and are signatures of the different damage/fault types. Image algorithms may use this library of data to deconvolve spatial frequency signatures to expose damage at specific structure locations. These patterns are then tagged with a specific colour. Accordingly, the image for that specific frequency slice, becomes a colour coded image. The final user image then combines these frequency slices to produce a 3D image.

In order to be processed, the acquired data requires interpretation (data 'diagnosis'). Data may be interpreted by software suitable for identifying patterns in the data. This may include 3D imaging methods as will be described in more detail below, as well as other image analysis methods. For example, image analysis methods for determining object features can be based on interpolation and demosaicing and other methods known in the art, any they may include low pass filters and Bayesian interpretation to reduce noise.

In order to aid interpretation, a library of damage/fault types, and their corresponding radio signatures may be compiled for reference. Fault types include cracks, strain/stress/fatigue, or temperature, among others. Furthermore, these methods may provide a measure of crystallinity within the composite material, which could be an important standard/metric to assess composite damage.

The management of data is needed for large-scale structures. Data management systems may be used to periodically log of the data at appropriate time intervals (much like a personal computer collects and logs its actions). For example, if tests are taken during this intervals, data may be logged two or three times a day. If tests are made in real-time then, data logging is more frequent. Inspection of the data log can then be useful for diagnosing any problems and flagging any pending issues.

A crucial part of being able to process the convoluted structural information from the evanescent field of the composite requires an understanding of the bulk electromagnetic field permeating the composite structure. It is noted that the internal field is determined by the structure of the composite, in particular its degree of crystalinity and order which may be diminished by damage (as was shown in FIG. 3).

In order to help deconvolute the structural information which is passed from the bulk to the evanescent field, the present inventors have compiled a library of electromagnetic signatures that were derived by building a virtual material from unit cells they have recognised in real composite materials. A Yee cell method known in the art (and represented in FIG. 16) was used to solve the electromagnetic field structure relation and to cover a broad frequency range, especially to low frequencies where the electromagnetic field is usually described by 'diffusion'. 'Diffusion' relates to the simplification of the electromagnetic interaction when the wavelength becomes very large, for example up to ten times greater than the original value. In this regime, the phase may be considered to be negligible. This simplification, however, may lead to defects visible as shadows in the obtain image. Advantageously, the Yee cell method does not require this simplification. This method, especially at low frequencies where diffusion applies, recovers the anisotropic conductivity of the material.

The Yee cell method comprises six time marching functions:

$$H_x|_{i,j,k}^{n+1/2} = D_a|_{i,j,k} \cdot H_x|_{i,j,k}^{n-1/2} + D_{b_z}|_{i,j,k} \cdot (E_y|_{i,j,k+1/2}^n - E_y|_{i,j,k-1/2}^n) -$$
$$D_{b_y}|_{i,j,k} \cdot (E_z|_{i,j+1/2,k}^n - E_z|_{i,j-1/2,k}^n)$$

$$H_y|_{i,j,k}^{n+1/2} = D_a|_{i,j,k} \cdot H_y|_{i,j,k}^{n-1/2} + D_{b_x}|_{i,j,k} \cdot (E_z|_{i+1/2,j,k}^n - E_z|_{i-1/2,j,k}^n) -$$
$$D_{b_z}|_{i,j,k} \cdot (E_x|_{i,j,k+1/2}^n - E_x|_{i,j,k-1/2}^n)$$

$$H_z|_{i,j,k}^{n+1/2} = D_a|_{i,j,k} \cdot H_z|_{i,j,k}^{n-1/2} + D_{b_y}|_{i,j,k} \cdot (E_x|_{i,j+1/2,k}^n - E_x|_{i,j-1/2,k}^n) -$$
$$D_{b_x}|_{i,j,k} \cdot (E_y|_{i+1/2,j,k}^n - E_y|_{i-1/2,j,k}^n)$$

$$E_x|_{i,j,k}^{n+1} = C_a|_{i,j,k} \cdot E_x|_{i,j,k}^n + C_{b_y}|_{i,j,k} \cdot (H_z|_{i,j+1/2,k}^{n+1/2} - H_z|_{i,j-1/2,k}^{n+1/2}) -$$
$$C_{b_z}|_{i,j,k} \cdot (H_y|_{i,j,k+1/2}^{n+1/2} - H_y|_{i,j,k-1/2}^{n+1/2})$$

$$E_y|_{i,j,k}^{n+1} = C_a|_{i,j,k} \cdot E_y|_{i,j,k}^n + C_{b_z}|_{i,j,k} \cdot (H_x|_{i,j,k+1/2}^{n+1/2} - H_x|_{i,j,k-1/2}^{n+1/2}) -$$
$$C_{b_x}|_{i,j,k} \cdot (H_z|_{i+1/2,j,k}^{n+1/2} - H_z|_{i-1/2,j,k}^{n+1/2})$$

$$E_z|_{i,j,k}^{n+1} = C_a|_{i,j,k} \cdot E_z|_{i,j,k}^n + C_{b_x}|_{i,j,k} \cdot (H_y|_{i+1/2,j,k}^{n+1/2} - H_y|_{i-1/2,j,k}^{n+1/2}) -$$
$$C_{b_y}|_{i,j,k} \cdot (H_x|_{i,j+1/2,k}^{n+1/2} - H_x|_{i,j-1/2,k}^{n+1/2})$$

FIG. 17 shows how various image planes containing structural information from different depths in a composite material are 'brought together' in the evanescent field and require deconvolution. The method shown in FIG. 17 for building up a 3D image involves taking images at a range of different frequencies and ascribing a decay function to each imaged feature. For example, a higher frequency may detect the surface features and present them more strongly in the obtained image, whereas lower frequencies detect less of the surface information and more of deeper interior structure in a relative sense. With this method, both the feature and its depth information may be extracted.

FIG. 18 represents an imaging method for obtaining stereoscopic images that can be used separately or in conjunction with the imaging methods described above. Half of the number of probes may be use to obtain a first image, Image 1, at one position, while the other half of the probes may be used to measure the image, Image 2, from a slightly displaced reference point equal to the separation between the probe elements. From Image 1 and Image 2, a stereoscopic image may be obtained using conventional stereoscopic techniques.

Composite materials typically consist of reinforcement and matrix, the reinforcement for aerospace and especially airliners typically being carbon fibre or Kevlar. The matrix is normally a thermosetting epoxy, or thermoplastic polyester, vinyl ester or nylon. The result is a carbon fibre-reinforced polymer or carbon fibre-reinforced plastic (CFRP or CRP). Typical aerospace applications for these advanced composites are ultra-high-performance pressure vessels, rocket motor cases, and launch tubes. For intrinsic sensor applications, a conductive fibre in a relatively insulating matrix produces a significant electrical periodicity that can be utilised by the method according to the present invention. Other reinforcement material choices which lead to a significant periodicity in the electrical properties include metals, semiconductors, composite particles (eg metals or insulators) or holes in the matrix.

Using an intrinsic sensing method according to the invention, one may gain rapid access to information about structural materials, both during manufacture and within the end application. The sensing is achieved conveniently at very low cost compared to current SHM systems and methods.

Typical changes in a property of composite materials representing defects of composite materials which may be detected with the present invention include fibre breaks, microcracks, delaminations, foreign objects or contaminants, impact damage, and porosity. The term porosity generally refers to the voids caused by the trapped air or the volatile gas that is released during the cure process. Matrix-dominated features, such as compressive strength, transverse tensile strength, and interlaminar shear strength for example are affected by porosity. It has generally been found that the interlaminar shear strength decreases by approximately 7% per 1% of voids, up to a total void content of about 7%.

Techniques for detecting porosity in composite materials may be broadly categorised as one of the following: direct imaging, correlation with a single ultrasonic frequency (narrow band approach), or correlation with ultrasonic frequency slope (broadband approach). The correlation with the frequency slope of the attenuation curve has been successfully demonstrated and has been widely applied. There also appears to be an approximately linear variation of slope as a function of increasing void content. Using the correlation between void content and the attenuation slope, void contents have been ultrasonically determined and compared with void contents that were determined destructively by acid digestion. Although the differences may be subtle, advanced imaging techniques such as the method according to the present invention aid in the determination of matrix-rich or matrix starved areas in the scanned specimen.

Furthermore, fibre/matrix distribution, fibre waviness, and fibre orientation are important microstructural properties of composites. A change in the environment of the particles can also occur due to creeping or instability within the material over time, which degrades the material's performance. All these properties may be detected well using methods according to the present invention.

The materials employed are typically construction materials where information on wear, damage or temperature is sought. Advantageously, regular composite materials may be employed so as to provide information on change in the environment of the material, such as a change in stress, strain, volume distortion, or density fluctuation. Furthermore, by developing models and software, one may correlate the returned signals to determine temperature, pH, hydration contamination, radiation or icing of the material.

Accordingly, the present invention has a number of important advantages. For example, it allows for continuous or selective collection of data concerning critical structural components, such as structural components for the aerospace industry (such as aircraft wings, panels, bolts, vessels and seals) and smart seals for the oil and gas industry, without the need for installing any extra sensors on or in the structure which can weaken the structure. As these intrinsic sensors use regular materials, in some cases, the intrinsic sensing materials are already available. For example certain carbon fibre laminate structures used for aerospace applications are quasi crystals.

This also presents a far more economical SHM system, reducing aircraft maintenance and repair costs in industries which increasingly use composite materials to form such structural components.

Existing methods for testing composite materials in aerospace engineering include for example ultrasonic transducers and a composite sample in a water bath to obtain 2D images, or the coin-tap method where the 'sound' is 'listened to'. Advantageously, the present invention allows for testing of such materials without the need to utilise a water bath. Furthermore, the test system according to the present invention can be miniaturized, and provides the advantage of portability. The present invention also has a low power consumption (only milliwats of power are required).

Another advantage of the present invention is that it allows for a very fast acquisition of data and the wear or fatigue status of the component can be collected in real time, so that the time of replacement is clear, and the downtime, control and operating costs in manufacturing and in use of the component are reduced. The manufacturing process can also be closely monitored and optimised with feedback from the interior of the material.

Further still, in the field of pipeline sensing, the system and method of the invention advantageously enable continuous strain monitoring, allowing operators to prevent problems such as leaks arising. By contrast, current fibre optic techniques recognise a "hot spot" or "cold spot" that indicates the presence of a leak in liquid or gas systems, respectively, only once the leak has occurred.

Another advantage of the invention is that it improves the robustness of monitoring systems, such as downhole monitoring, removing the need for connectors and wires. The need for sensor devices to have separate power sources is also removed, as power is provided to the sensing elements via wireless interactions. Other application areas include composite quality control, aircraft and high speed automobile brake systems, civil structures or human health monitoring, pressure monitoring in nuclear and chemical plants, temperature measurement of heat shields and nose cones, and crack detection in space stations, railway lines and tankers.

For reliability in harsh environments, the present invention can make use of the structure as a sensor. A good example is measurement of water viscosity inside a pipe. A composite aircraft wing incorporating intrinsic sensing adhesives at surfaces mating the skin with the support frame. These areas are often hotspots of stress in panels or other load bearing structures, and convey information on their mechanical status. For this reason, key mechanical information for a composite structure is available at the bonding points.

The invention claimed is:

1. A sensing system comprising:
a material comprising a matrix and a plurality of non-insulating particles substantially equally spaced within the matrix such that the composite material has coherent electrical periodicity in at least one dimension resulting in periodic conductivity or a periodic dielectric constant, wherein the non-insulating particles do not have microwave resonance and are purely reflective; and
a receiver arranged to receive a source RF signal from an RF source for interrogating the material and a returned RF signal wherein the returned RF signal is reflected from the non-insulating particles to produce the returned RF signal;
wherein interrogating the material comprises exciting the material into an electromagnetic field mode to generate an evanescent surface field profile at the surface of the material and coupling the source RF signal to the generated evanescent surface field profile, thereby achieving efficient energy transfer to the material;
wherein a change in the position of one or more of the non-insulating particles causes the returned RF signal to change, such that a change in the crystallinity of the material is determined from the returned RF signal.

2. The system according to claim 1 wherein the matrix is a non-conductive matrix and the non-insulating particles are conducting particles.

3. The system according to claim 2, wherein the conductive particles include at least one of carbon particles, carbon fibre, graphenes, aluminium particles, silver particles, copper particles, gold particles, and carbon nanotubes.

4. The system according to claim 1, wherein the non-insulating particles are semiconducting particles.

5. The system according to claim 1, wherein the non-insulating particles are composite particles comprising a metal and an insulator.

6. The system according to claim 1, wherein the matrix comprises a polymer.

7. The system according to claim 6, wherein the matrix comprises at least one of a thermosetting epoxy, thermoplastic polyester, vinyl ester or nylon.

8. The system according to claim 1, wherein a change in the returned RF signal is any of a change in amplitude, a change in frequency, a phase-shift, or a change in interference effects.

9. The system according to claim 1, wherein the change in the crystallinity of the material is any of a particle break, a microcrack, a delamination, a contaminant, matrix impact damage, or a change in porosity.

10. The system according to claim 1, wherein the receiver is arranged to receive ambient RF signals.

11. A method of sensing a change in a property of a material, the material comprising a matrix and a plurality of non-insulating particles substantially equally spaced within the matrix such that the composite material has coherent electrical periodicity in at least one dimension resulting in periodic conductivity or a periodic dielectric constant, wherein the non-insulating particles do not have microwave resonance and are purely reflective, the method comprising the steps of:
interrogating the material with a source RF signal from an RF source so as to excite the material into an electromagnetic field mode to generate an evanescent surface field profile at the surface of the material and couple the source RF signal to the generated evanescent surface field, thereby achieving efficient energy transfer to the material;
receiving a returned RF signal wherein the returned RF signal is reflected from the non-insulating particles; and
determining the change in the crystallinity of the material from a change in the returned RF signal that is caused by a change in the position of one or more of the non-insulating particles.

12. The method according to claim 11, wherein interrogating the material comprises scanning the surface of the material using a single mechanical probe.

13. The method according to claim 11, wherein interrogating the material comprises scanning the surface of the material with an electronic multiple probe along a 1D or 2D path.

14. The method according to claim 11, wherein interrogating the material further comprises scanning the surface field profile using an electronic multiple probe.

15. The method of claim 11, wherein interrogating the material further comprises scanning the surface field profile using a 2D probe array with electronic switching or multiple signal channels.

16. The method according to claim 15, further comprising placing the 2D probe array in a flexible probe sheet.

17. The method according to claim 11, wherein the source RF signal is modulated.

18. The method according to claim 11, wherein the material is obtained by doping a semiconductor material.

19. The method according to claim 11, wherein the material comprises a plurality of cells and wherein each cell represents an antenna element.

20. The method according to claim 19, wherein the plurality of cells are coupled and form a cell array.

21. The method according to claim 20, wherein the plurality of cells coupled via induced modulated RF currents.

22. The method according to claim 15, wherein the 2D probe array comprises at least one high impedance probe.

23. The method according to claim 22, wherein the at least one high impedance probe comprises a plurality of metal micro-elements.

24. The method according to claim 22, wherein the at least one high impedance probe is a diode rectifier or a gate of a field effect transistor.

25. The method according to claim 11, wherein the returned RF signal is received by a homodyne receiver.

26. The method according to claim 19, wherein the plurality of cells form a wireless cellular network.

27. The method or system according to claim 11, wherein determining the change in the crystallinity of the material comprises 2D or 3D imaging of the composite material.

28. The method or system according to claim 11, wherein determining the change in the crystallinity of the material comprises detecting an anisotropic conductivity of the material.

* * * * *